United States Patent
DiMatteo

(10) Patent No.: US 6,217,600 B1
(45) Date of Patent: Apr. 17, 2001

(54) THROMBUS FILTER WITH BREAK-AWAY ANCHOR MEMBERS

(75) Inventor: Kristian DiMatteo, Maynard, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/491,272

(22) Filed: Jan. 26, 2000

(51) Int. Cl.[7] ................................................. A61B 17/04
(52) U.S. Cl. ........................... 606/202; 606/191; 606/198
(58) Field of Search .................................. 606/200, 194, 606/198, 191

(56) References Cited

U.S. PATENT DOCUMENTS

| | | |
|---|---|---|
| 3,952,747 | 4/1976 | Kimmell, Jr. . |
| 4,494,531 | 1/1985 | Gianturco ............................. 128/1 R |
| 4,688,553 | 8/1987 | Metals .................................. 128/1 R |
| 4,727,873 | 3/1988 | Mobin-Uddin . |
| 4,781,177 | 11/1988 | Lebigot ................................. 128/897 |
| 4,793,348 | 12/1988 | Palmaz . |
| 4,817,600 | 4/1989 | Herms et al. . |
| 5,059,205 | 10/1991 | El-Nounou et al. .................. 606/200 |
| 5,133,733 | 7/1992 | Rasmussen et al. .................. 606/200 |
| 5,147,379 | 9/1992 | Sabbaghian et al. ................. 606/206 |
| 5,234,458 | 8/1993 | Metais ................................... 606/200 |
| 5,242,462 | 9/1993 | El-Nounou et al. .................. 606/200 |
| 5,324,304 | 6/1994 | Rasmussen ............................ 606/200 |
| 5,344,427 | 9/1994 | Cottenceau et al. .................. 606/200 |
| 5,370,657 | * 12/1994 | Irie . |
| 5,383,887 | 1/1995 | Nadal ................................... 606/200 |
| 5,681,347 | 10/1997 | Cathcart et al. ...................... 606/200 |
| 5,709,704 | 1/1998 | Nott et al. ............................ 606/200 |
| 5,713,917 | * 2/1998 | Leonhardt ............................ 606/194 |
| 5,911,704 | 6/1999 | Humes .................................. 604/93 |
| 5,954,741 | * 9/1999 | Fox ...................................... 606/198 |

* cited by examiner

*Primary Examiner*—Gary Jackson
(74) *Attorney, Agent, or Firm*—Crompton, Seager & Tufte, LLC

(57) ABSTRACT

A thrombus filter which can be securely fixed at a selected location in the vascular system of a patient and removed when no longer required. The thrombus filter includes a body portion and a plurality of struts, each strut having a joined end and a free end. The joined end of each strut is fixably attached to the body portion. The struts radiate outwardly from the body member such that the thrombus filter is generally conical in shape. The free end of each strut includes an anchor member. A weakened portion is disposed proximate the free end of each strut. When removal of the thrombus filter is desired, forces are applied to the thrombus filter causing the struts to break at the weakened portions proximate the free ends. When breaking of the struts has been accomplished, the thrombus filter may be freely pulled into the lumen of the retrieval catheter. Once the thrombus filter is disposed inside the lumen of the retrieval catheter, the removal of the thrombus filter from the body of the patient becomes a simple matter of withdrawing the retrieval catheter from the blood vessel.

19 Claims, 9 Drawing Sheets

THROMBUS FILTER WITH BREAK-AWAY ANCHOR MEMBERS

FIELD OF THE INVENTION

The present invention relates generally to filters for use inside blood vessels. More particularly, the present invention relates to thrombus filters which can be securely affixed at a selected location in the vascular system and removed when no longer required.

BACKGROUND OF THE INVENTION

There are a number of situations in the practice of medicine when it becomes desirable for a physician to place a filter in the vascular system of a patient. One of the most common applications for vascular filters is the treatment of Deep Venous Thrombosis (DVT). Deep Venous Thrombosis patients experience clotting of blood in the large veins of the lower portions of the body. These patients are constantly at risk of a clot breaking free and traveling via the inferior vena cava to the heart and lungs. This process is known as pulmonary embolization. Pulmonary embolization can frequently be fatal, for example when a large blood clot interferes with the life-sustaining pumping action of the heart. If a blood clot passes through the heart it will be pumped into the lungs and may cause a blockage in the pulmonary arteries. A blockage of this type in the lungs will interfere with the oxygenation of the blood causing shock or death.

Pulmonary embolization may be successfully prevented by the appropriate placement of a thrombus filter in the vascular system of a patient's body. Placement of the filter may be accomplished by performing a laparotomy with the patient under general anesthesia. However, intravenous insertion is often the preferred method of placing a thrombus filter in a patient's vascular system.

Intravenous insertion of a thrombus filter is less invasive and it requires only a local anesthetic. In this procedure, the thrombus filter is collapsed within a delivery catheter. The delivery catheter is introduced into the patient's vascular system at a point which is convenient to the physician. The delivery catheter is then fed further into the vascular system until it reaches a desirable location for filter placement. The thrombus filter is then released into the blood vessel from the delivery catheter.

In the treatment of Deep Venous Thrombosis, a thrombus filter is placed in the inferior vena cava of a patient. The inferior vena cava is a large vessel which returns blood to the heart from the lower part of the body. The inferior vena cava may be accessed through the patient's femoral vein.

Thrombus filters may be placed in other locations when treating other conditions. For example, if blood clots are expected to approach the heart and lungs from the upper portion of the body, a thrombus filter may be positioned in the superior vena cava. The superior vena cava is a large vessel which returns blood to the heart from the upper part of the body. The superior vena cava may by accessed through the jugular vein, located in the patient's neck.

Once placed inside a blood vessel, a thrombus filter acts to catch and hold blood clots. The flow of blood around the captured clots allows the body's lysing process to dissolve the clots.

The walls of the blood vessels are lined with a thin inner membrane or intima. When the anchor portions of a thrombus filter puncture this inner membrane the body responds to a puncture of the intima with a process known in the art as neointimal hyperplasia. As a result, the punctured area of inner membrane is overgrown with a number of new cells. The anchor portions of the thrombus filter are typically encapsulated with new cell growth (neointimal hyperplasia). Because the portions of the filter contacting the blood vessel wall become fixed in this way, it is impractical to remove many prior art filters percutaneously after they have been in place for more than two weeks.

There are a number of situations in which it may be desirable for a physician to remove a thrombus filter. If the physician determines that more effective filtering would occur with a thrombus filter in a different position, the physician may remove the original filter from its present positions and deploy a new filter in a new position. If the physician determines that the risk of blood clots forming is no longer present, it may be desirable to remove the thrombus filter completely. Thrombus filters are often used in conjunction with anticoagulation drugs. At some point, the physician may desire to discontinue the use of anticoagulation drugs. The physician may also want to remove the thrombus filter in conjunction with discontinuing the anticoagulation drugs. The removal of the thrombus filter from the patient eliminates any possibility that a compete occlusion will occur at the thrombus filter site. The removal of the thrombus filter also eliminates any possibility that the thrombus filter will become loose and migrate within the blood vessel. A loose thrombus filter is undesirable because it may migrate to a dangerous or life threatening position.

SUMMARY OF THE INVENTION

The present invention pertains to a thrombus filter and a method of removing a filter using minimally invasive methods avoiding complications due to neointimal encapsulation of anchor portions of the filter. The thrombus filter includes a body member and a plurality of elongated struts. Each strut has a joined end and a free end. The joined end of each strut is fixably attached to the body member. The struts radiate outwardly from the body member such that the thrombus filter is generally conical in shape. When the thrombus filter is deployed inside a blood vessel, the free ends of the struts engage the blood vessel wall. The body member of the thrombus filter is held in a position proximate the center of the blood vessel by the plurality of struts which engage the blood vessel walls with opposing force vectors.

When the thrombus filter is disposed in a blood vessel, the conical formation of struts acts to trap or capture blood clots. The generally conical shape of the formation of struts serves to urge captured blood clots toward the center of the blood flow. The flow of blood around the captured clots allows the body's natural lysing process to dissolve the clots.

To assure firm attachment of the thrombus filter to the blood vessel walls, anchor portions may be formed at the free ends of the struts. These anchor portions typically include one or more bends and one or more sharp points. A weakened portion is disposed proximate the free end of each strut. The weakened portion of each strut may include notches, grooves, holes and the like.

When removal of the thrombus filter is desired, a removal catheter with a lumen and a distal end is disposed inside the blood vessel. The removal catheter enters the patient's vascular system at a point which is readily accessible to the physician. Once in the vascular system, the removal catheter is urged forward until the distal end of the catheter is proximate the thrombus filter. The distal end of the removal catheter is then urged forward so that the body member of the thrombus filter is disposed inside the lumen of the removal catheter. A force is applied to the thrombus filter urging the body member further into the lumen of the removal catheter. The magnitude of this force is sufficient to break the struts of the thrombus filter at the weakened portions proximate the free ends of the struts. When the struts are broken, the thrombus filter may be pulled freely into the lumen of the removal catheter. Removal of the thrombus filter from the body of the patient then becomes a matter of simply withdrawing the removal catheter from the blood vessel. The anchor members of the thrombus filter remain attached to the walls of the blood vessel by encapsulating cell growth due to neointimal hyperplasia.

An alternate method of removal involves repeatedly deflecting the struts with a force which is not of sufficient magnitude to break the struts of the thrombus filter at the outset. However, the repeated deflection of the struts causes fatigue cracks to grow at the weakened portions. As described above, the cross sectional area of each strut is reduced at a weakened portion including slots, holes, and the like. The cross sectional area of the struts is further reduced by fatigue cracking due to repeated deflection of the struts. After multiple deflections, the cross sectional area of the struts, at the weakened areas will be small enough that a small force alone is sufficient to break the struts at the weakened areas.

DETAILED DESCRIPTION OF THE INVENTION

The following detailed description should be read with reference to the drawings, in which like elements in different drawings are numbered identically. The drawings which are not necessarily to scale, depict selected embodiments and are not intended to limit the scope of the invention.

Examples of constructions, materials, dimensions, and manufacturing processes are provided for selected elements. All other elements employ that which is known to those of skill in the field of the invention. Those skilled in the art will recognize that many of the examples provided have suitable alternatives which may be utilized.

Figure 1:
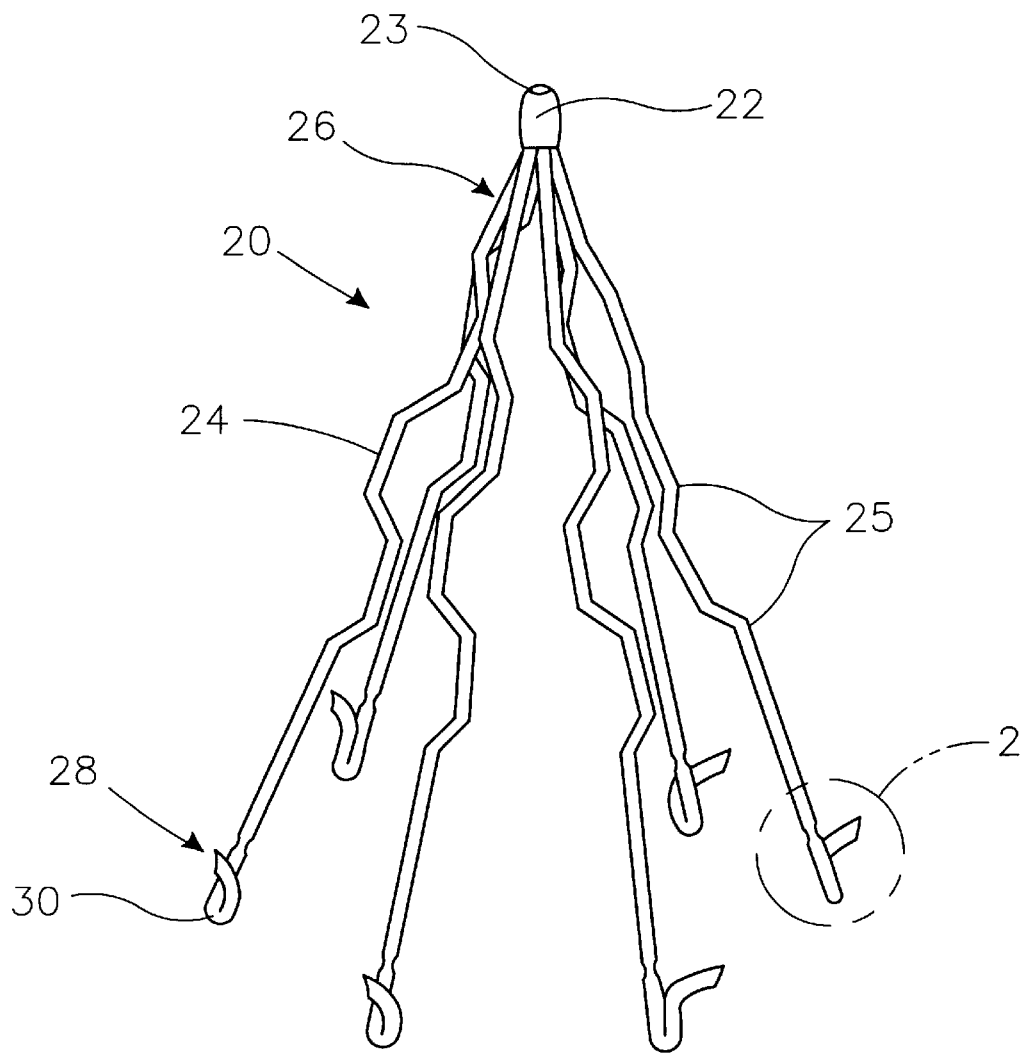
FIG. 1 is a perspective view of a thrombus filter.

FIG. 1 is a perspective view of a thrombus filter 20. Thrombus filter 20 includes a body member 22 and a plurality of elongated struts 24. Struts 24 each have a joined end 26 and a free end 28. Joined end 26 of each strut 24 is fixedly attached to body member 22.

Struts 24 may be fabricated from wire with a circular or rectangular cross section. For example, struts 24 may be comprised of 2 inch lengths of 0.018" diameter wire. Stainless steel, titanium, and nickel-titanium alloys have all been found to be acceptable materials for struts 24. In the embodiment of FIG. 1, a plurality of bends 25 are disposed between free end 28 and fixed end 26 of each strut 24. It should be understood that struts 24 may also be straight, or include bends different than those illustrated in FIG. 1, without departing from the spirit of scope of the present invention.

In the embodiment of FIG. 1, body member 22 is generally cylindrical in shape, and includes a bore 23. It should be under stood that other embodiments of body member 22 are possible without departing from the spirit or scope of the present invention.

Struts 24 radiate outwardly from body member 22 such that thrombus filter 20 is generally conical in shape. When thrombus filter 20 is deployed inside a blood vessel, free ends 28 engage the blood vessel wall. Body member 22 is held in a position proximate the center of the blood vessel by the plurality of struts 24 which engage the blood vessel walls with opposing force vectors.

When thrombus filter 20 is disposed in a blood vessel, the conical formation of struts 24 acts to trap, or capture blood clots. The generally conical shape of the formation of struts 24 serves to urge captured blood clots toward the center of the blood flow. The flow of blood around the captured blood clots allows the body's natural lysing process to dissolve the clots.

Figure 2:
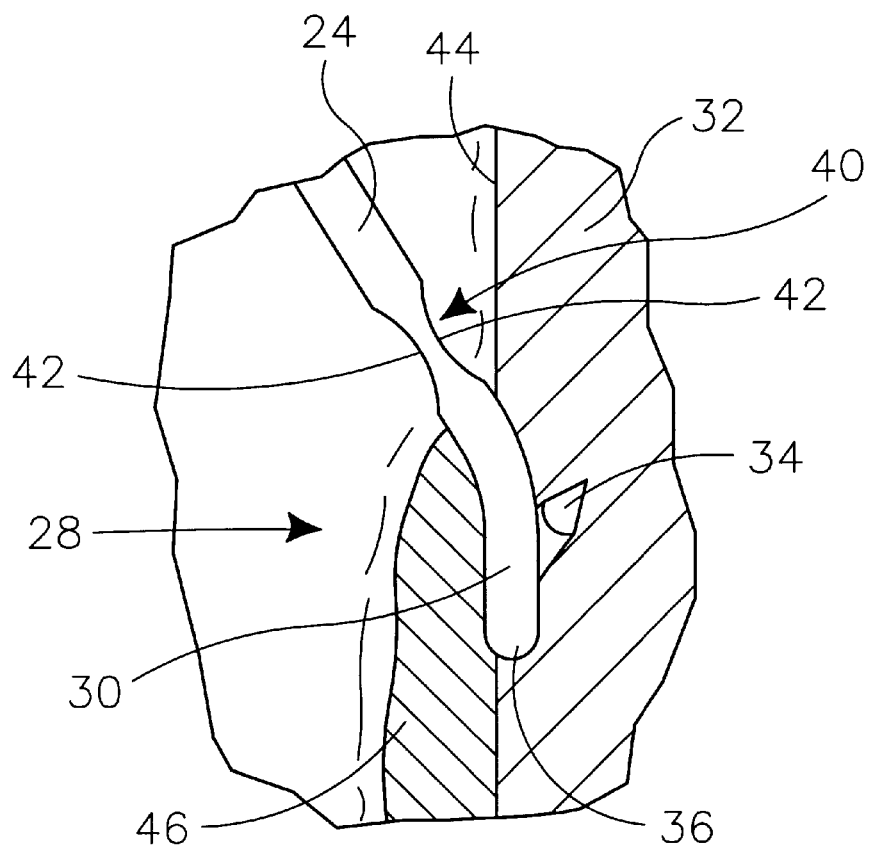
FIG. 2 is a plan view of the anchor portion of a thrombus filter.

To assure firm attachment of thrombus filter 20 to the blood vessel walls, anchor portions 30 may be formed at free ends 28 of struts 24. FIG. 2 illustrates one embodiment of an anchor portion 30 embedded in a vessel wall 32. Anchor portion 30 includes a sharp point 34 and a bend 36. Strut 24 includes a weakened portion 40 disposed proximate free end 28. In the particular embodiment of FIG. 2 weakened portion 40 includes a plurality of divets 42. Divets 42 substantially reduce the cross sectional area of strut 24 at weakened portion 40. Divets 42 may be fabricated by removing material from strut 24 with a removal process such as machining or grinding.

Divets 42 may also be fabricated by displacing material with a process such as metal forming or crimping.

Blood vessel wall 32 is lined with a thin inner membrane or intima 44. When anchor portion 30 is embedded in wall 32 it punctures inner membrane 44. The body responds to a puncture of inner membrane 44 with a process known in the art as neointimal hyperplasia. The punctured area of inner membrane 44 is overgrown with a number of new cells. Referring again to FIG. 2, it can be seen that anchor portion 30 of strut 24 is covered with encapsulating cell growth 46.

Figure 3:
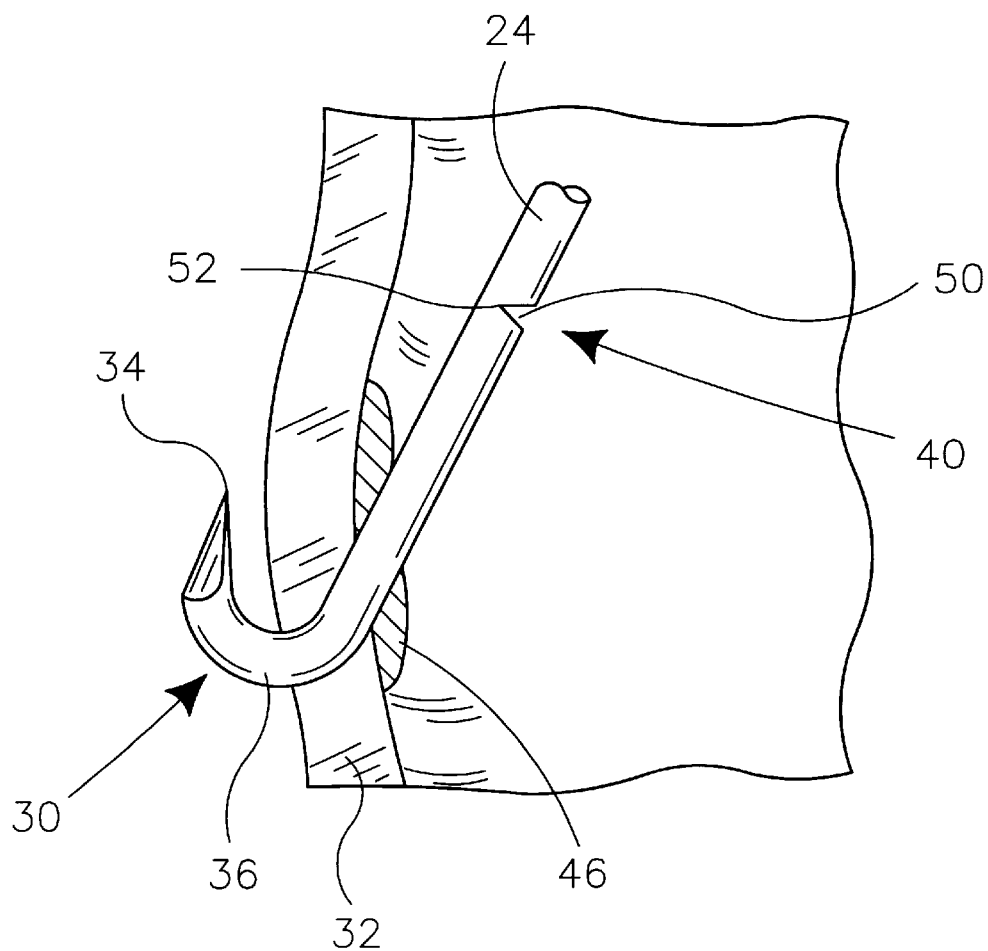
FIG. 3 is a plan view of an alternate embodiment of the anchor portion of a thrombus filter.

FIG. 3 is a plan view of strut 24 including alternate embodiments of anchor portion 30 and weakened portion 40. Anchor portion 30 includes sharp point 34 and bend 36. In FIG. 3 sharp point 34 has penetrated vessel wall 32. Weakened portion 40 of strut 24 includes a notch 50. Notch 50 substantially reduces the cross sectional area of strut 24 at weakened portion 40. Notch 50 can terminate in a sharp point 52 which serves to concentrate stresses which are applied to weakened portion 40 of strut 24. Notch 50 may be produced by any one of several material removal processes including, but not limited to: grinding, milling and broaching. Alternately, notch 50 may be fabricated using a material deformation process. As in the previous embodiment, it can be seen in FIG. 3 that anchor portion 30 of strut 24 is covered with encapsulating cell growth 46.

Figure 4:
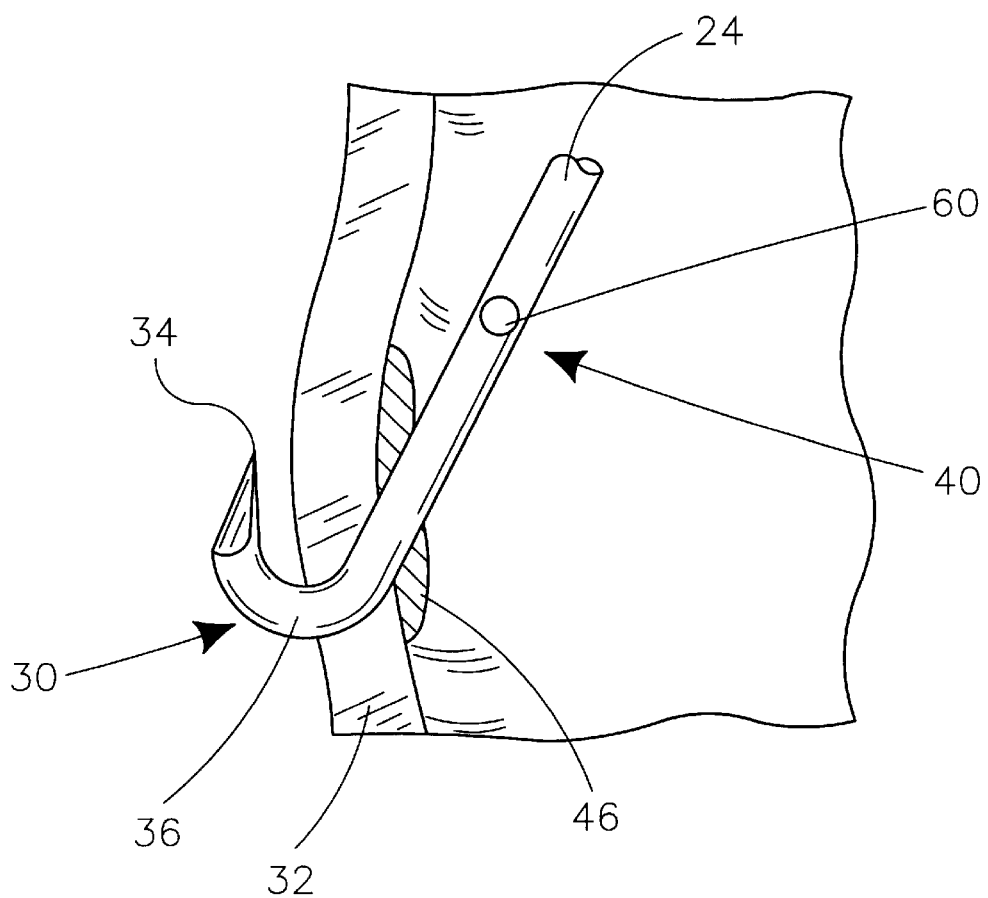
FIG. 4 is a plan view of an alternate embodiment of the anchor portion of a thrombus filter.

FIG. 4 is a plan view of strut 24 illustrating an additional embodiment of weakened portion 40. In this embodiment, weakened portion 40 includes a hole 60 which substantially reduces the cross-sectional area of strut 24 at weakened portion 40. Hole 60 may be produced using any one of several material removal process including: drilling, LASER drilling, and electronic discharge machining. In FIG. 4, hole 60 is shown as a "through hole" passing completely through strut 24. It should be understood that other embodiments of hole 60 may be used without deviating from the spirit and scope of the present invention. For example, hole 18 could be a blind hole, or weakened portion 40 could include a plurality of holes.

As described above, the body responds to the presence of thrombus filter 20 with a process referred to as neointimal hyperplasia. The result is that the anchor portions 30 of struts 24 will become covered with encapsulating cell growth 46. Within about 2 to 3 weeks after thrombus filter 20 is implanted, anchor portions 30 of struts 24 will be completely encapsulated by encapsulating cell growth 46. With many prior art thrombus filters, removal of the filter after neointimal hyperplasia encapsulation has occurred is very difficult, if not impossible.

It is desirable that the thrombus filter of the present invention can be removed using minimally invasive methods without complications due to neointimal hyperplasia encapsulation of anchor portions 30 of struts 24. A process which may be utilized to remove thrombus filter 20 from a blood vessel 90 is schematically represented in FIG. 5.

Figure 5:
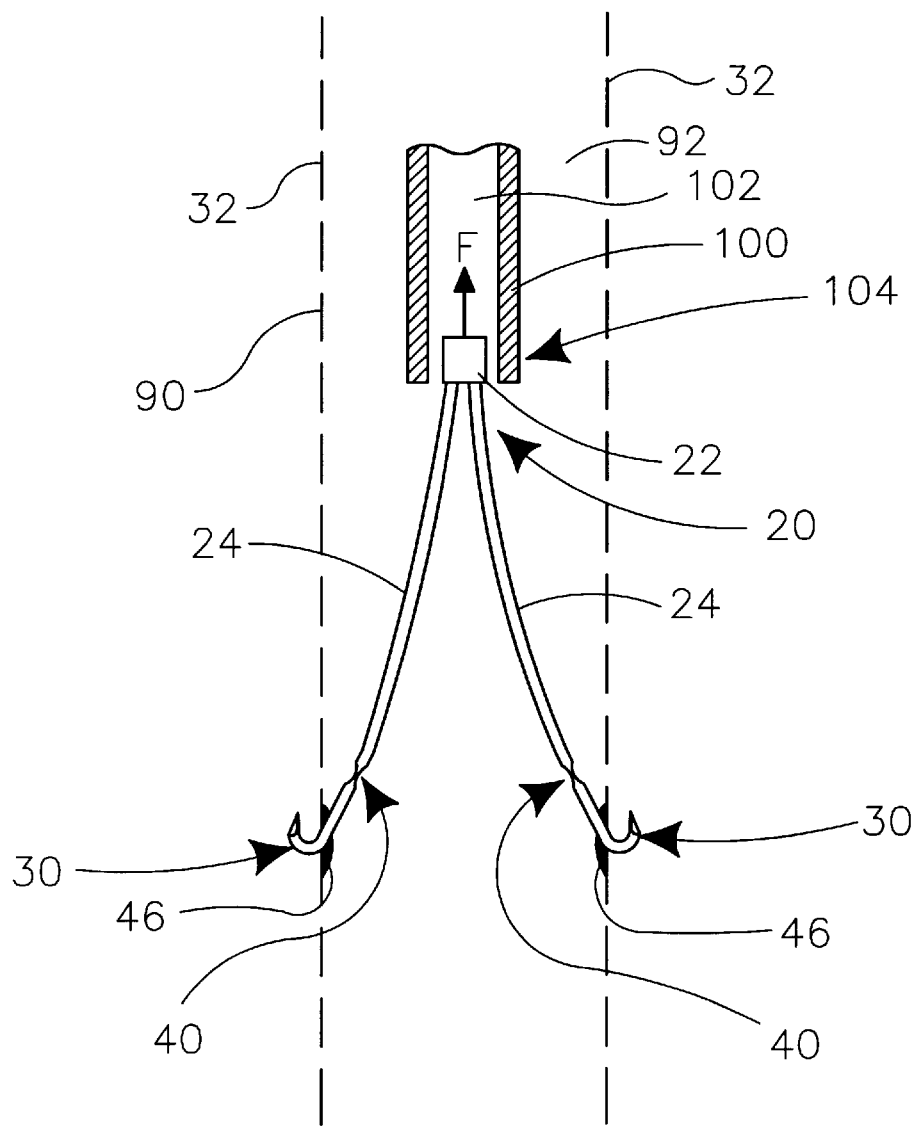
FIG. 5 is a schematic representation of a removal process for use with a thrombus filter.

FIG. 5 schematically illustrates a blood vessel 90 including a lumen 92 and walls 32. Thrombus filter 20 is disposed in lumen 92 of blood vessel 90. Anchor portions 30 of struts 24 are embedded in walls 32 of blood vessel 90. Neointimal hyperplasia has resulted in encapsulating cell growth 46 proximate anchor portions 30 of struts 24.

A removal catheter 100 with a lumen 102 and a distal end 104 is also disposed in lumen 92 of blood vessel 90. Removal catheter 100 enters the patient's vascular system at a point which is readily accessible to the physician. Once in the vascular system, catheter 100 is urged forward until distal end 104 is proximate thrombus filter 20. For example, if thrombus filter 20 is located in the inferior vena cava of a patient's vascular system, removal catheter 100 may enter the vascular system at the femoral vein. Alternately, if thrombus filter 20 is located in the superior vena cava of a patient's vascular system, removal catheter 100 may enter the vascular system at the jugular vein. In either case, the filter removal procedure can be minimally invasive, and not require general anesthesia.

Distal end 104 of removal catheter 100 is urged forward so that body member 22 of thrombus filter 20 is disposed inside lumen 102 of removal catheter 100. A force F is applied to thrombus filter 20 urging body member 22 further into lumen 102 of removal catheter 100. The magnitude of force F is of sufficient magnitude to break struts 24 at weakened portions 40. When struts 24 are broken at weakened portions 40 thrombus filter 20 including struts 24 may be pulled into lumen 102 of removal catheter 100. Removal catheter 100 may then be removed from the body of the patient by withdrawing removal catheter 100 from blood vessel 90. Thus, thrombus filter 20 is removed from blood vessel 100 but anchor members 30 remain attached to walls 32 by encapsulating cell growth 46.

Figure 6:
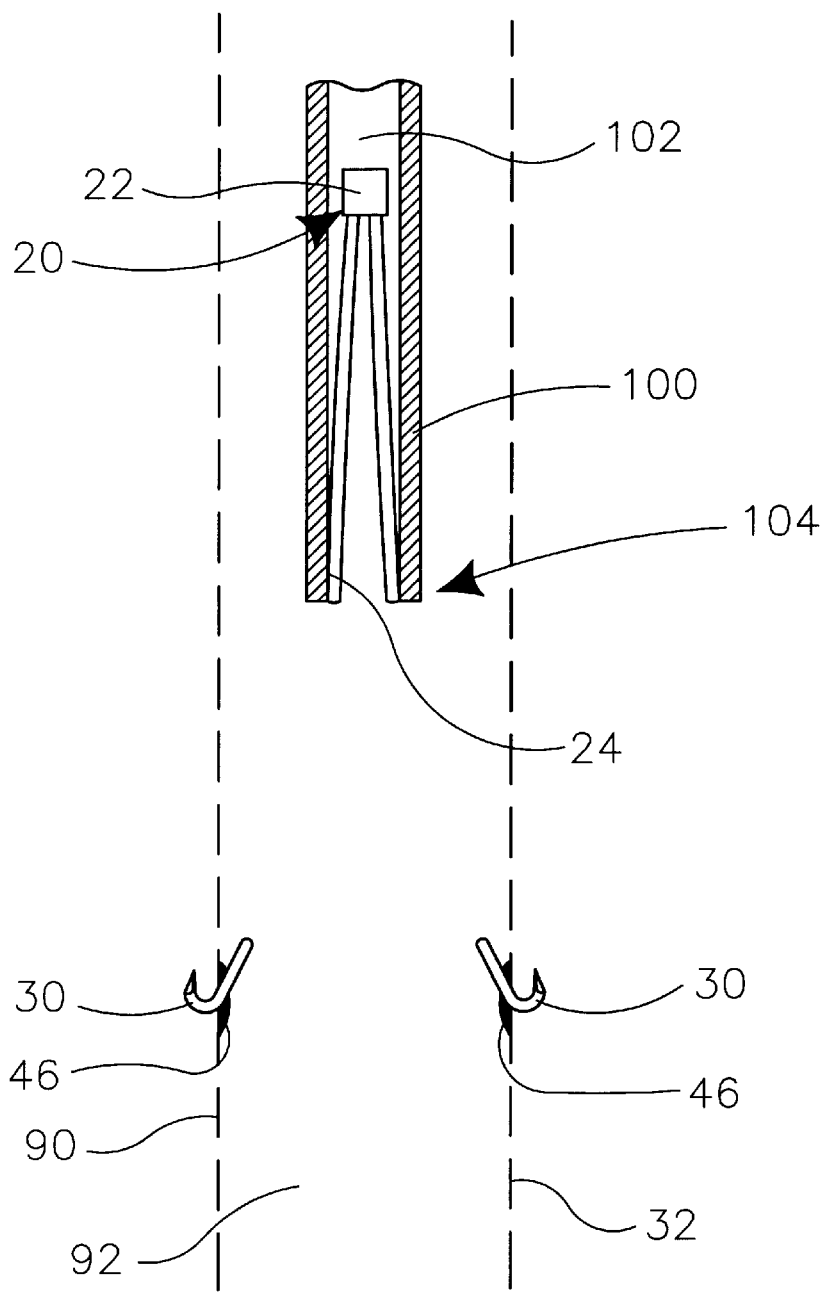
FIG. 6 is a schematic representation of a thrombus filter drawn into the lumen of a removal catheter.

FIG. 6 is a schematic representation of thrombus filter 20 after it has been pulled into lumen 112 of retrieval catheter 110. As may be seen in FIG. 6, pulling thrombus filter 20 into lumen 112 of retrieval catheter 110 causes struts 24 to collapse. When struts 24 are collapsed, retrieval catheter 110 may be withdrawn from blood vessel 100. As can also be seen in FIG. 6, anchor members 30 remain fixed in the walls of blood vessel 100, retained by encapsulating cell growth 46.

Force F may be applied to thrombus filter 20 using a variety of methods. For example, the pulling of thrombus filter 20 into lumen 112 of retrieval catheter 110 may be accomplished with a retrieval wire including a hook. The retrieval wire may pass through bore 23 of body member 22. With the retrieval wire disposed in bore 23 of body member 22, the hook may engage body member 22 so that a pull force can be applied to thrombus filter 20.

Struts 24 may also be intentionally broken at weakened portions 40 by repeatedly deflecting struts 24 to induce fatigue cracking at weakened portions 40. The magnitude of the force required for this removal method is less than the magnitude of force required to break struts 24 without fatigue cracking.

A number of methods may be used to deflect struts 24. First, a pull force may be applied to thrombus filter 10 as shown in FIG. 5. Applying a pull force to thrombus filter 20 deflects blood vessel walls 32 and struts 24. When the pull force is released, blood vessel walls 32 and struts 24 deflect a second time in returning to an unstressed position. Pulling force F may be applied and released repeatedly to induce fatigue cracking at weakened areas 40. It should be noted that the pull force applied when using this removal method is not sufficient to break struts 24 at the outset. However, multiple applications of force F cause fatigue cracks to grow at weakened areas 40. As described above the cross-sectional area of struts 24 is reduced at weakened areas 40 by slots, holes, and the like. The cross-sectional area of struts 24 is further reduced by fatigue cracking due to repeated applications of force F. After multiple applications of force F, the cross-sectional area of struts 24 at weakened areas 40 will be small enough that force F alone is sufficient to break struts 24 at weakened areas 40.

Figure 7:
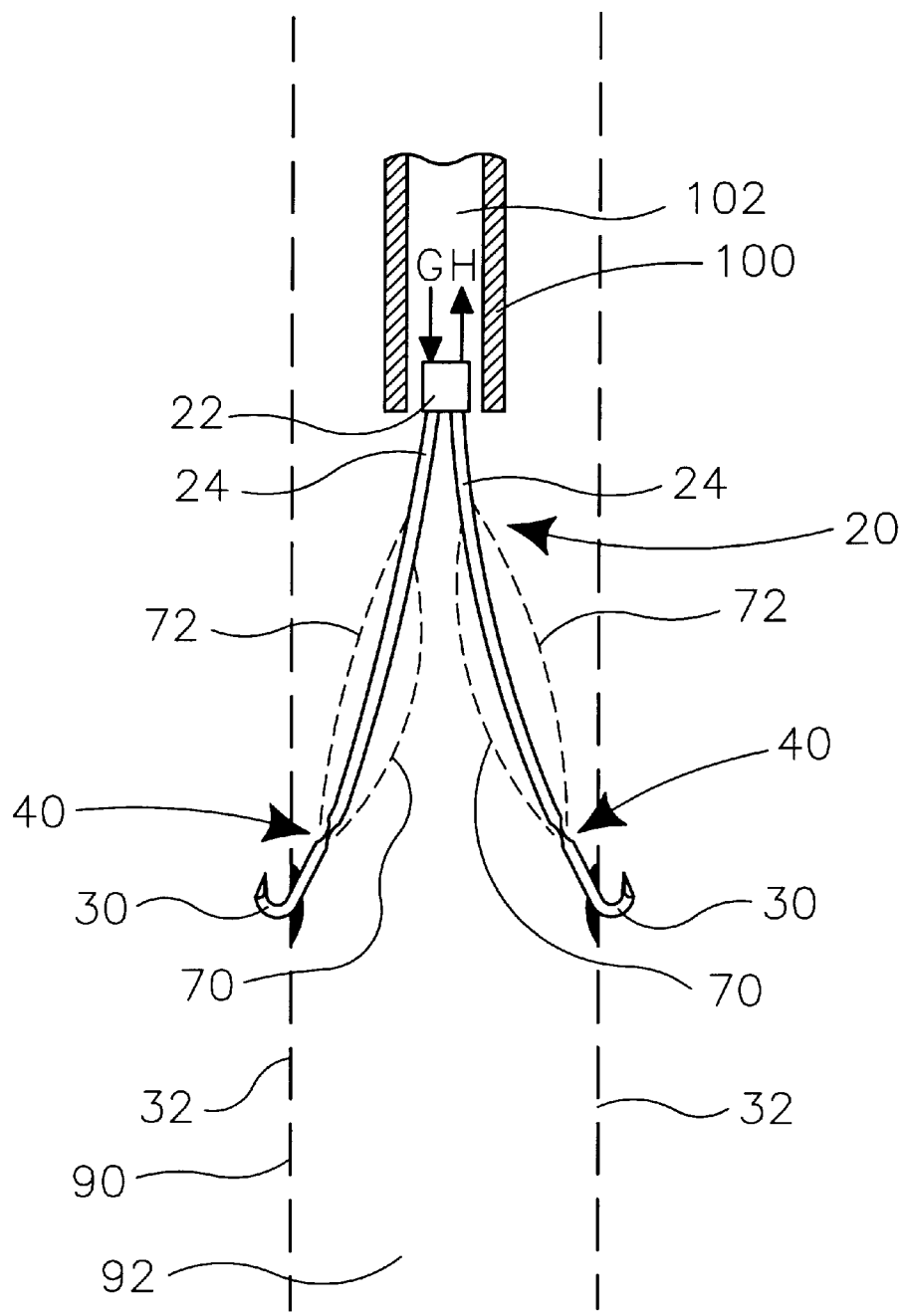
FIG. 7 is a schematic representation of an alternate removal process for use with a thrombus filter.

Fatigue cracking may also be induced in struts 24 by alternately applying pushing and pulling forces to body member 22 of thrombus filter 20. FIG. 7 is a schematic representation of a removal method utilizing a pushing force G and a pulling force H. Pushing force G and pulling force H may be transferred to body member 22 of thrombus filter 20 using an elongated force transfer member (not shown) disposed inside removal catheter 100. Force transfer member preferably is substantially rigid in the longitudinal direction.

Applying a push force to thrombus filter 20 deflects struts 24 to a first stressed position 70. Pulling on thrombus filter 20 deflects struts 24 to a second stressed position 72. In FIG. 7, First stressed position 70 and second stressed position 72 are represented by hidden lines. Alternating between pushing force G and pulling force H causes fatigue cracks to grow at weakened areas 40 of struts 24. As discussed above, the fatigue cracks continue to grow until forces G & H alone are sufficient to break struts 24 at weakened points 40. Thrombus filter 20 may then be pulled into lumen 102 of removal catheter 100 and subsequently removed from lumen 92 of blood vessel 90.

In the embodiment of FIG. 7, pushing force G and pulling force H are applied to thrombus filter 20 by the force transfer member. To accomplish this, a mechanical link is formed between the force transfer member and body portion 22 of thrombus filter 20. This mechanical link may be formed using a number of methods. For example, the distal end of the force transfer member 110 may include a hook which interlinks with a mating hook fixably attached to body portion 22 of thrombus filter 20.

Figure 8:
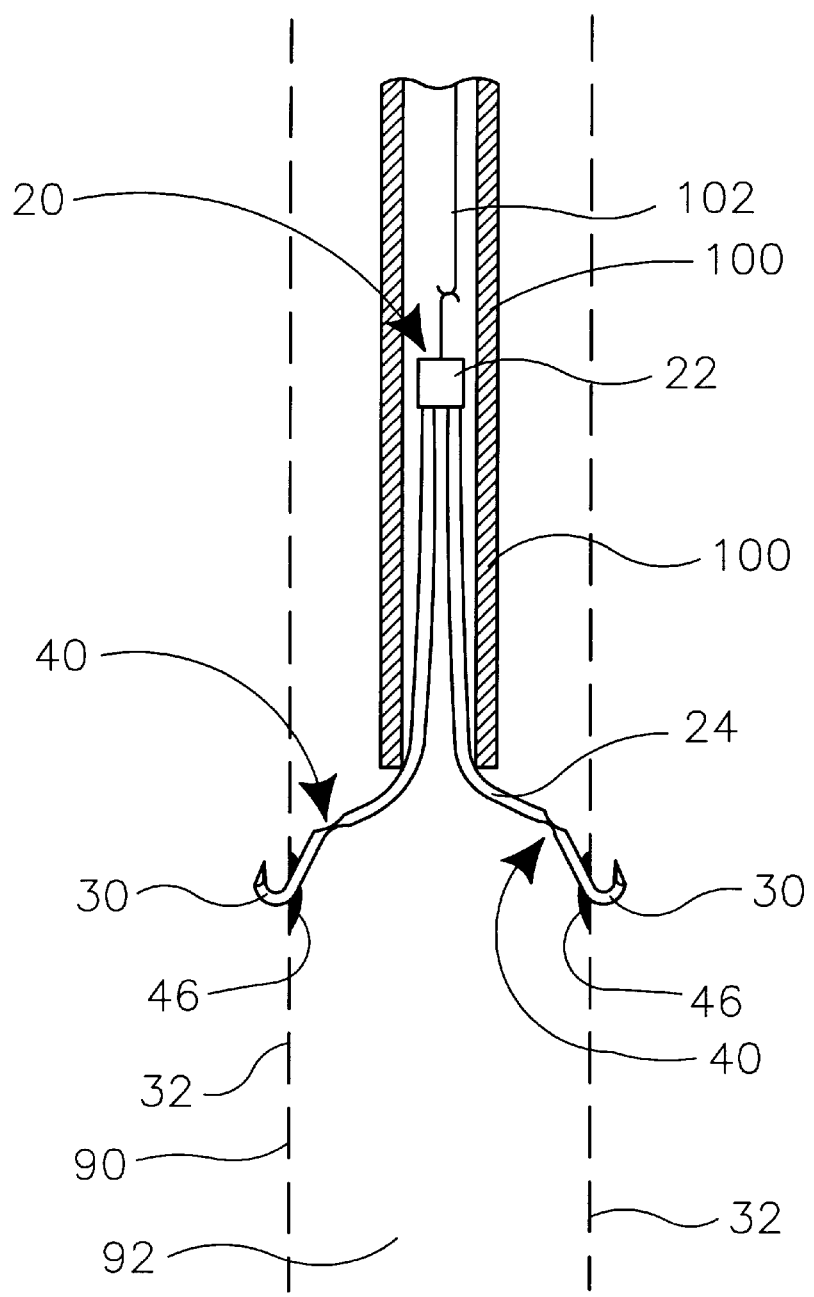
FIG. 8 is a schematic representation of an alternate removal process for use with a thrombus filter.

Struts 24 may also be deflected by applying a pulling force to thrombus filter 20 while simultaneously applying a pushing force to removal catheter 100. This method of removing thrombus filter 20 is schematically illustrated in FIG. 8. Pushing removal catheter 100 over thrombus filter 20 causes struts 24 to deflect as shown in FIG. 8. When catheter 100 is pushed over thrombus filter 20, struts 24 are deflected to a stressed position. When catheter 100 is pulled back, struts 24 are free to return to an unstressed position. Repeated cycling results in the growth of fatigue cracks until struts 24 break at weakened portions 40.

Figure 9:
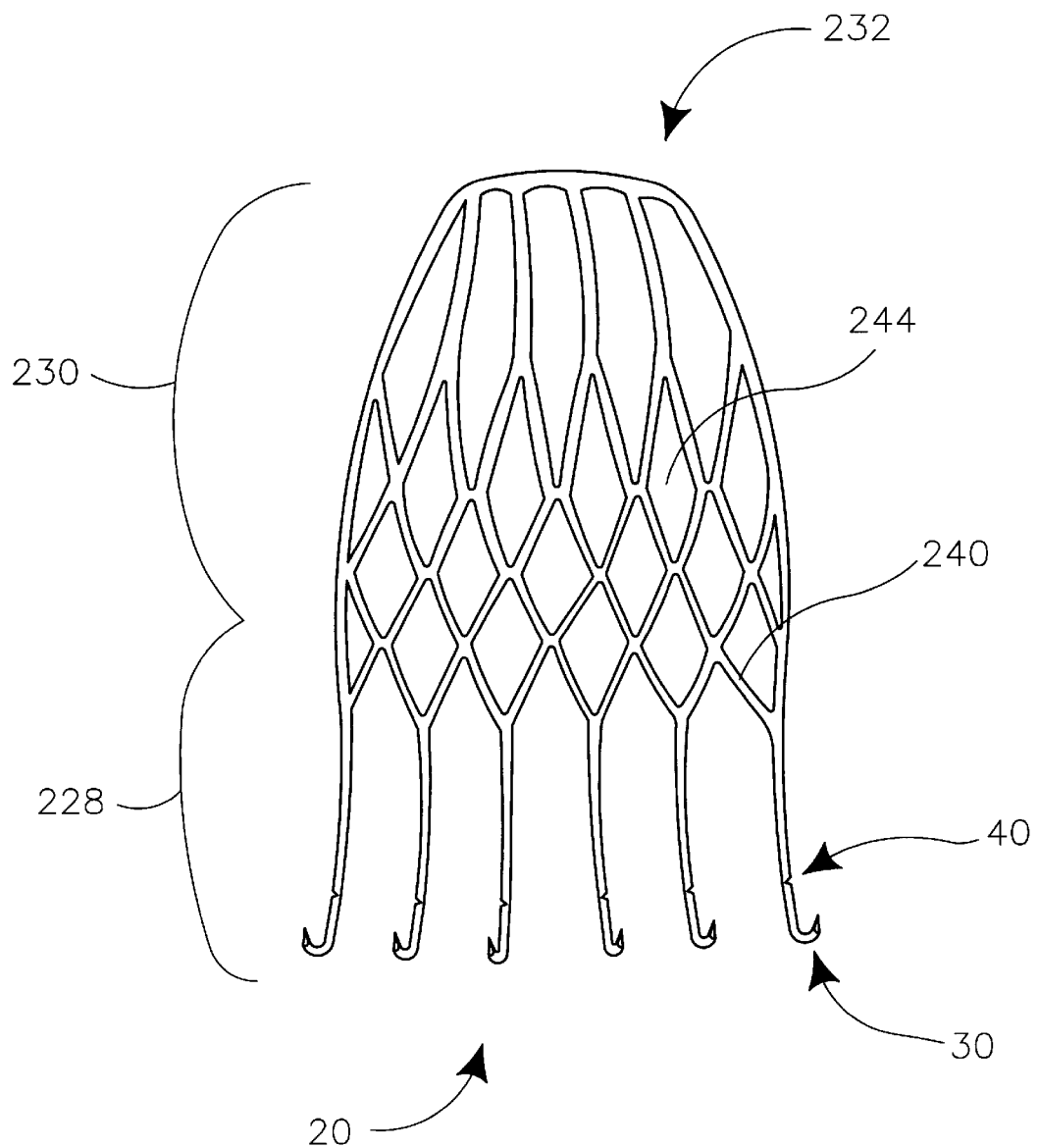
FIG. 9 is a plan view of an additional embodiment of a thrombus filter in accordance with the present invention.

Those with skill in the art will appreciate that many embodiment of thrombus filter 20 are possible without deviating from the spirit or scope of the present invention. FIG. 9 is a plan view illustrating an additional embodiment of a thrombus filter 20 in accordance with the present invention. Thrombus filter 20 includes a generally cylindrical anchoring portion 228, and a generally conical filtering portion 230 terminating at an apex 232.

Filtering portion 230 includes a plurality of elongated strands 240 arranged in a latticework pattern to create a plurality of filtering cells 244. Filtering cells 244 allow blood to flow through filtering portion 230 with little resistance. Cells 244 also enable filtering portion 230 to trap, or capture blood clots traveling though a blood vessel. The generally conical shape of filtering portion 230 urges captured blood clots toward the center of the blood flow. The flow of blood around the captured blood clots allows the body's natural lysing process to dissolve the clots.

Referring again to FIG. 9, it may be appreciated that strands 240 extend beyond filtering portion 230 into anchoring portion 228. Each strand 240 of anchoring portion 228 may include an anchor 30. In a presently preferred embodiment, anchor members 30 include a sharp point capable of penetrating the walls of a blood vessel. In this fashion, anchor members 30 reduce the likelihood that thrombus filter 20 will migrate upstream or downstream in the lumen of the blood vessel. A weakened portion 40 is disposed proximate each anchor 30.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A thrombus filter configured for placement within a blood vessel lumen defined by a blood vessel wall, comprising:
    a body portion;
    a plurality of struts, each strut having a joined end and a free end;
    the joined end of each strut being fixedly attached to the body portion; and
    each strut including a weakened portion proximate the free end of the strut.

2. The thrombus filter of claim 1, wherein the free end of each strut includes a sharp projection.

3. The thrombus filter of claim 1, wherein each strut is rectangular in cross section.

4. The thrombus filter of claim 1, wherein each strut is circular in cross section.

5. The thrombus filter of claim 1, wherein the cross-sectional area of the strut is reduced proximate the weakened portion.

6. The thrombus filter of claim 1, wherein the weakened portion includes a notch.

7. The thrombus filter of claim 1, wherein the weakened portion includes a slot.

8. The thrombus filter of claim 1, wherein the weakened portion includes a hole.

9. A thrombus filter configured for placement within a blood vessel lumen defined by a blood vessel wall, comprising:
    a body portion;
    a plurality of struts, each strut having a joined end and a free end;
    the joined end of each strut being fixedly attached to the body portion;
    the free end of each strut including an anchor member; and
    each strut including a weakened portion proximate the anchor member.

10. The thrombus filter of claim 9, wherein the struts have a circular cross section.

11. The thrombus filter of claim 9, wherein the struts have a rectangular cross section.

12. The thrombus filter of claim 9, wherein the weakened portion includes a notch.

13. The thrombus filter of claim 9, wherein the weakened portion includes a slot.

14. The thrombus filter of claim 9, wherein the weakened portion includes a hole.

15. The thrombus filter of claim 9, wherein the free end of each strut includes a sharp projection.

16. A method of removing a thrombus filter from a blood vessel lumen inside a living being, the method comprising the steps of:
    providing a thrombus filter including a plurality of struts, each strut having a free end;
    the free end of each strut including an anchor member, and each strut including a weakened portion proximate the anchor member;
    connecting a retrieval catheter to the thrombus filter;
    breaking each strut proximate the weakened portion; and
    withdrawing the filter from the vessel.

17. The method of claim 16, wherein each anchor member includes a sharp projection.

18. The method of claim 12, further including the step of applying a force to the thrombus filter, wherein the force applied is sufficient in magnitude to break the struts proximate the weakened portion.

19. The method of claim 12, further including the step of repeatedly deflecting the struts to induce fatigue cracking at the weakened portions of the struts.

* * * * *